US006268174B1

(12) United States Patent
Neuman et al.

(10) Patent No.: US 6,268,174 B1
(45) Date of Patent: Jul. 31, 2001

(54) METHOD OF STABLE INTEGRATION OF DNA INTO NEURONS

(75) Inventors: Toomas Neuman, Santa Monica; Howard O. Nornes, Fort Collins, both of CA (US)

(73) Assignee: Spinal Cord Society, Fergus Falls, MN (US)

( * ) Notice: Subject to any disclaimer, the term of this patent is extended or adjusted under 35 U.S.C. 154(b) by 0 days.

(21) Appl. No.: 08/933,977

(22) Filed: Sep. 19, 1997

Related U.S. Application Data

(60) Provisional application No. 60/026,348, filed on Sep. 19, 1996.

(51) Int. Cl.[7] .......................... C12P 21/06; C12N 15/85; C12N 15/02; C07H 21/04
(52) U.S. Cl. ............................. 435/69.1; 435/6; 435/7.1; 435/320.1; 435/455; 435/458; 435/490; 536/23.1
(58) Field of Search .................. 435/6, 320.1, 172.5, 435/172.3, 948, 455, 458, 465, 490, 7.1; 935/77, 78, 36, 39, 66; 536/23.1

(56) References Cited

U.S. PATENT DOCUMENTS 5,501,979 * 3/1996 Geller et al. ....................... 435/320.1
5,763,217 * 6/1998 Cynader et al. ..................... 435/69.1

OTHER PUBLICATIONS

Freed et al., "Intrastriatal adrenal medulla grafts in rats," J. Neurosurg, 65: 664–670 (1986).
Lindvall et al., "Transplantation in Parkinson's Disease: Two Cases of Adrenal Medullary Grafts to the Putamen," Annals of Neurology, 22:4 (Oct. 1987), pp. 457–468.
Levi–Montalcini, "The Nerve Growth Factor 35 Years Later," Science, 237:1154–61 (Sep. 4, 1987).
Hansen et al., "Adrenal Medullary Autografts into the Basal Ganglia of Cebus Monkeys: Graft Viability and Fine Structure," Experimental Neurology, 102:65–75 (1988).
Hofer et al., "Brain–derived neurotrophic factor prevents neuronal death in vivo," Nature, 331:261–262 (Jan. 21, 1988).
Goetz et al., "Multicenter Study of Autologous Adrenal Medullary Transplantation to the Corpus Striatum in Patients With Advanced Parkinson's Disease," N. Engl. J. Med., 320:337–341 (1989).
Alderson et al., "Brain–Derived Neurotrophic Factor Increases Survival and Differentiated Functions of Rat Septal Cholinergic Neurons in Culture," Neuron. 5:297–306 (1990).
Phillips et al., "BDNF mRNA Is Decreased in the Hippocampus of Individuals with Alzheimer's Disease," Neuron, 7:695–702 (Nov. 1991).

Tuszynski et al., "Recombinant Human Nerve Growth Factor Infusions Prevent Cholinergic Neuronal Degeneration in the Adult Primate Brain," Ann. Neurol, 30:625–636 (1991).
Barbareschi et al., "p53 Protein expression in central nervous system neoplasms," J. Clin. Pathol, 45:583–586 (1992).
Yan et al., "Brain–derived neurotrophic factor rescues spinal motor neurons from axotomy–induced cell death," Nature, 360:753–755 (Dec. 1992).
Terry, "Regeneration in Alzheimer Disease and Aging," Advances in Neurology, 59:1–4 (1993).
Koliatsos et al., "Evidence That Brain–Derived Neurotrophic Factor Is a Trophic Factor for Motor Neurons In Vivo," Neuron, 10:359–367 (Mar. 1993).
Oberholtzer et al., "Molecular Cloning of a Chick Cochlea cDNA Encoding a Subunit of DNA Replication Factor C/Activator 1," DNA and Cell Biol., 13:857–863 (1994).
Okada et al., "Proliferating cell nuclear antigen in neurons: induction by u.v. irradiation," NeuroReport, 7(11) (Jul. 1996), pp. 1770–72.
Copy of International Search Report dated Dec. 2, 1997.
Murnane et al., "Recombination events during integration of transfected DNA into normal human cells," Nucleic Acids Research, 18:9 (1990), pp. 2733–38.
Tsurimoto et al., "Replication Factors Required for SV40 DNA Replication in Vitro," The Journal of Biological Chemistry, 266:3 (1991), pp. 1950–60.
Hunting et al., "DNA polymerase delta mediates excision repair in growing cells damaged with ultraviolet radiation," Biochem. Cell Biol, vol. 69 (1991), pp. 303–308.
Chun et al., "The Recombination Activating Gene–1 (RAG–1) Transcript Is Present in the Murine Central Nervous System," Cell, vol. 64 (Jan. 11, 1991), pp. 189–200.
Coverley et al., "A role for the human single–stranded DNA binding protein HSSB/RPA in an early stage of nucleotide excision repair," Nucleic Acids Research, 20:15 (1992), pp. 3873–80.
Melendy et al., "An Interaction between Replication Protein A and SV40 T Antigen Appears Essential for Primosome Assembly during SV40 DNA Replication," Journal of Biological Chemistry, 268:5 (Feb. 15, 1993), pp. 3389–95.
Hübscher et al., "DNA Replication and Chemotherapy," Physiological Reviews, 74:2 (Apr. 1994), pp. 259–303.
Podust et al., "Assembly of DNA polymerase δ and ε holoenzymes depends on the geometry of the DNA template," Nucleic Acids Research, 22:15 (1994), pp. 2970–75.

* cited by examiner

Primary Examiner—Stephanie Zitomer
(74) Attorney, Agent, or Firm—Patterson, Thuente, Skaar & Christensen, P.A.

(57) ABSTRACT

The invention relates to the stable transfection of neurons with DNA encoding proliferating cell nuclear antigen (PCNA) and replication factor C (RFC). Also, co-transfection of a functional gene along with the DNA encoding PCNA and RFC causes stable integration of the functional gene.

14 Claims, No Drawings

METHOD OF STABLE INTEGRATION OF DNA INTO NEURONS

This application claims the benefit of U.S. Provisional Application Ser. No. 60/026,348, entitled "A Method of Stable Integration of DNA Into Neurons," filed Sep. 19, 1996, which is hereby specifically incorporated by reference.

BACKGROUND AND SUMMARY OF THE INVENTION

The advancement of our understanding of molecular genetics has lead to possibilities of treating diseases with gene-based therapies. Two major technical issues for efficient application of gene therapies is the delivery of the gene into the target cells and efficient, long-term expression of the gene. Likely the best strategy to achieve long-term expression of introduced gene will be to integrate introduced DNA into the genome of cell. The present inventors have developed a method which will increase significantly the efficiency of integration of introduced DNA into the genome of differentiated neurons.

The present inventors developed and tested a method which is based on the use of proteins involved in stimulation of the DNA repair and recombination process to integrate introduced DNA into adult neurons. DNA repair is carried out by DNA polymerases $\delta$ (pol $\delta$) and $\epsilon$ (pol $\epsilon$). These polymerases are stimulated by proliferating cell nuclear antigen (PCNA), replication protein A (RPA), and replication factor C (RFC) under various conditions (Hunting et al., Biochemistry and Cell Biology, 69:303–308 (1991), Tsurimoto and Stillman, J. Biol. Chem., 266:1950–1960 (1991), Coverley et al., Nucleic Acids Research, 20:3873–3880 (1992), Melendy and Stillman, J. Biol. Chem., 268:3389–3395 (1993), Podust et al., Nucleic Acids Research, 22:2970–2975 (1994), Hübscher and Spadari, Physiological Rev., 74:259–303 (1994)). The same factors participate also in the process of DNA recombination. DNA damage caused by UV or gamma ray irradiation stimulates repair processes by inducing the expression of several repair proteins as well as activating enzymatic activities. Integration of foreign DNA occurs by a mechanism similar to that used for repair of spontaneous or gamma ray-induced strand breaks (Murnane, et al., Nucl. Acids Res., 18:2733–2738 (1990)).

Levels of proteins that are involved in DNA repair are very low in the adult neurons. For example, expression of PCNA, RPA and RFC are almost undetectable in adult neurons. On the other hand, several components that are necessary for high efficiency recombination are expressed in neurons. For example, recombination activating gene RAG1 which is involved in the V(D)J gene recombination is expressed in many areas of the CNS (Chun et al., Cell, 64:189–200 (1991)). The present inventors propose that overexpression of proteins that are important components of repair and recombination system will result in increased integration of introduced DNA.

The homology between the DNA repair and recombination factors from different species (from yeast to human) is very high, which predicts that mechanisms operating in the regulation of these processes are similar in different species.

The present inventors have shown that transfecting neurons with DNA encoding PCNA and RFC large subunit in combination with UV treatment stimulates stable integration of introduced DNA into cortical neurons in vitro. The present inventors have also shown that such transfection in vitro can be applied to stably integrate a functional gene(s) by simultaneous cotransfection of the genes encoding PCNA and RFC with the functional gene(s).

Without being bound by any particular theory of how PCNA and RFC large subunit facilitate DNA integration, the present inventors hypothesize that by inducing DNA repair and recombination in differentiated neurons, the present invention provides for the stable production of specific proteins in neurons. With stable and functional integration of a therapeutic or functional gene, the present invention also provides for gene therapy in which normally differentiated neurons are induced to produce a given therapeutic protein.

The present invention is directed use of proteins involved in stimulation of DNA repair and recombination in neurons, which provides for production of proteins, peptides, or polypeptides (for simplicity, the term "protein" is used to encompass all of these materials) in neurons, for gene therapy that provides proteins in neurons. According to the present invention, stable integration of delivered genes into the genome of neurons is accomplished. This novel method is based on the transfection of the postmitotic neurons with DNAs which are known to induce DNA repair and recombination, along with DNA which has potential therapeutic effect.

DETAILED DESCRIPTION OF PREFERRED EMBODIMENTS

The present inventors demonstrated that introduced DNA expression was stable for weeks. With stable integration of the delivered gene into the genome of the target neurons, this method of gene transfer provides for gene therapy for neurodegenerative diseases such as Parkinson's, Huntingtons and Alzheimers and for reconstruction following trauma and stroke. Further, this method can be used for gene transfer to any nonproliferating and fully differentiated cell of the body, since regulation of the DNA repair and recombination is not unique in the neuronal cells and, likely, induction of DNA repair and recombination will result in stable integration of cotransfected DNA.

According to certain embodiments, the invention involves transfection and expression of DNA repair and recombination factors (for example, PCNA and large subunit of RFC) that stimulate DNA repair and recombination in differentiated target cells, in combination with UV irradiation to induce DNA repair and recombination. There are many factors that stimulate DNA repair and recombination that may be used in the present invention.

Since both UV and gamma ray irradiation stimulate DNA repair and recombination processes then it will be possible to use X-ray irradiation instead of UV irradiation in the present invention. According to certain embodiments, dosages of X-ray irradiation for in vitro use, may include exposing cell culture to a cesium ($^{137}$Cs) irradiator at doses of about 10 to about 900 rad (1 rad equals 0.01 Gy). Humans and animals may be X-ray irradiated using an X-ray generator and different dose levels from 0.2 Gy to 50 Gy. According to certain preferred embodiments, irradiation will be focused on the treated area. Human and animal dosages may be calculated on results of in vitro experiments and by in vivo experiments as well.

According to certain embodiments, X-rays or other UV irradiation may not be necessary. Moreover, other means of damaging DNA to induce DNA repair and reconstruction may be employed according to certain embodiments.

Foreign DNA encoding therapeutically relevant proteins may be cotransfected during the induced DNA repair and recombination phase, which accomplishes a stable and functional integration of genes into neurons of different organisms including humans. This method provides gene-based therapies of the central nervous system (CNS).

For example, for Parkinson's disease, cDNA encoding tyrosine hydroxylase, which is key enzyme in the synthesis of L-DOPA and dopamine, can be introduced into cathecholamine producing neurons. For other neurodegenerative diseases and for stroke and trauma patients, genes expressing neurotrophic factors and their receptors can be introduced to promote regeneration.

According to certain embodiments, a single vector containing both PCNA and RFC nucleic acid is used to transfect the differentiated cell for inducing DNA synthesis. According to certain embodiments, the invention provides methods for inducing DNA synthesis in a differentiated cell that include transfecting a differentiated cell with nucleic acid encoding proliferating cell nuclear antigen (PCNA) and nucleic acid encoding replication factor C (RFC) and expressing the nucleic acid in the differentiated cell. According to certain embodiments, the invention provides methods for expressing a nucleic acid encoding a desired protein in a differentiated cell that include transfecting a differentiated cell with nucleic acid encoding proliferating cell nuclear antigen (PCNA), with nucleic acid encoding replication factor C (RFC), and with nucleic acid encoding a desired protein and expressing the nucleic acid encoding proliferating cell nuclear antigen (PCNA), the nucleic acid encoding replication factor C (RFC), and the nucleic acid encoding a desired protein.

The following example illustrates the invention. This example is for illustrative purposes only and is not intended to limit the scope of the invention.

EXAMPLE 1

Integration of Introduced DNA into Cortical
Neurons After Stimulation of DNA Repair and
Recombination Process In Vitro The procedure described in Example 1 uses proteins that are known to induce DNA repair and recombination in postmitotic neurons to achieve stable integration of DNA was tested using mouse cortical neurons. Cerebral cortexes of 17 day old mice embryos were dissociated into single cells after incubation in 0.25% trypsin, 1 mM EDTA for 15 minutes at 37° C. Trypsin digestion was stopped by DMEM plus 10% fetal calf serum containing 0.1% DNase. Cells ($3-4 \times 10^5$/ml) were cultured on poly-L-lysine (5 $\mu$g/cm$^2$) and collagen (100 $\mu$g/ml) coated 4 chamber culture slides (Lab-Tek) in Neurobasal medium (Gibco) containing B27 supplement (Gibco). Cytidine arabinoside (10 $\mu$M) was present in culture media during days 2–4 to block proliferation of non-neuronal cells. After 8 days in culture, cells were transfected using LipofectAMINE™ reagent according to the manufacturer's protocol (Gibco BRL Life Technologies) using 5 $\mu$g of pRcCMVneo eukaryotic expression vector (Invitrogen), lacZ cDNA cloned into pRcCMVneo (pRcCMV-lacZ), E2F1 cDNA cloned into pRcCMVneo (pRcCMV-E2F1), E1A$^{135}$ cDNA cloned into pRcCMVneo (pRcCMV-E1A$^{135}$), PCNA cDNA cloned into pRcCMVneo (pRcCMV-PCNA), or RFC cDNA cloned into pRcCMVneo (pRcCMV-RFC) cDNAs in 1 ml of the LipofectAMINE™. PCNA cDNA was obtained from Dr. Williams and it has Gene Bank Accession No. X57800. RFC large subunit cDNA was obtained from Dr. Luckow and it is described, including the nucleic acid sequence information, in Luckow et al., Molecular and Cellular Biology, 14:1626–1634 (1994). E2F1 cDNA was obtained from Dr. Helin and it has Gene Bank Accession No. M96577. E1A$^{135}$ was obtained from Dr. Morain. lacZ cDNA was obtained from Dr. Gruss.

The cells were exposed to the DNA for 3–5 hours in Neurobasal media and then placed in neurobasal growth media (GIBCO). Twelve hours after transfection, the cells were irradiated with a General Electric G8T5 germicidal lamp emitting predominantly 254-nm light at an incident rate of 0.35 J/m$^2$/s. After irradiation, fresh neurobasal culture media (GIBCO) containing B27 supplement was added.

Cortical neurons isolated from embryonic day 17 mice embryos differentiate and maintain a differentiated state in vitro. After 8 days in culture no DNA synthesis was detected in cortical neurons based on 5-bromo-2'-deoxyundine (BrdU) incorporation. To determine if the DNA delivered into differentiated cortical neurons is stably integrated and functional, the pRcCMV-lacZ discussed above was cotransfected with the pRcCMV-E2F1, pRcCMV-E1A$^{135}$, pRcCMV-PCNA, and pRcCMV-RFC discussed above. Transfected cells were analyzed 3 days and 3 weeks after transfection for lacZ expression using X-gal staining. Three days after transfection, all treatment groups showed very similar number of lacZ positive cells, which is an indication that transfection efficiencies were similar in all cultures (close to 1 %). After three weeks, control cultures did not contain any lacZ expressing cells. Over-expression of PCNA and RFC large subunit, in combination with UV treatment, results in stable integration of introduced DNA into cortical neurons in 10% of positively transfected cells. These results also demonstrated that efficiency of DNA integration into the genome of neurons is almost 10 times higher after stimulation of DNA repair and recombination processes compared to induction of S phase of the cell cycle by E1A and E2F (Table 1).

TABLE 1

Integration of lacZ into the genome of neurons using long term cultures of cortical neurons

| treatment | number of lacZ positive cells | |
|---|---|---|
| | after 3 days | after 3 weeks |
| none | 3218 ± 203 | 0 |
| E1A + E2F1 | 3756 ± 312 | 31 ± 7 |
| PCNA + RFC | 3257 ± 297 | 103 ± 11 |
| PCNA + RFC + UV irradiation | 3196 ± 301 | 327 ± 29 |
| UV irradiation | 3154 ± 342 | 5 ± 3 |

The present inventors also analyzed DNA integration using polymerase chain reaction (PCR) and Southern blot of genomic DNA of transfected neurons. Quantitation of PCR and Southern blot analyses using Phosphorimager technology demonstrated that PCNA+RFC+UV treated cells contain almost 10 times more lacZ DNA than E1A+E2F1 treated cells, and no lacZ DNA was detected in control cells.

EXAMPLE 2

Use of Proteins Known to Stimulate DNA Repair
and Recombination and Integration of DNA into
Adult Neurons In Vivo Cortical neurons will be transfected with plasmids expressing PCNA and RFC. The net result of this double transfection will be integration of cointroduced DNA into genome of neurons.

Adult rats (over 6 weeks) will be anesthetized using ketamine (85 mg/kg) and xylazine (13 mg/kg). Stereotaxic surgery will be performed to inject 10 μg of pRcCMV-PCNA/pRcCMV-RFC/cDNA which will be integrated in the same vector mixture (1:1:1) into the parietal cortex of adult rats. Injections will be made 4 mm posterior to the bregma, 5–5.5 mm lateral to the midline, and 3.0–3.5 mm depth in the parietal cortex over a five minute period and the needle will remain in place for an additional 10 minutes. Immunoliposomes will be prepared as described elsewhere in U.S. patent application No. 08/362,495, filed Jan. 10, 1995, which is incorporated by reference herein. Liposomes will be diluted to a concentration of 1 mg/ml total lipid. Plasmid DNA and Thy 1.1 antibody concentrations will be 0.025 mg/ml and 0.25 mg/ml, respectively. Cerebral cortexes of animals will be X-ray irradiated 1–3 days after surgery using dose levels from 0.2 Gy to 50 Gy.

Transfected brains will be analyzed 3 days, 7 days, 3 weeks, 2 months, and 6 months after transfection for β-galactosidase expression using X-gal staining at pH higher than 7.5. This staining minimizes visualization of endogenous galactosidases and stains the transfected β-gal cDNA will be transfected alone, without PCNA and RFC cDNAs.

EXAMPLE 3

Integration Of Tyrosine Hydroxylase (TH) cDNA Into Postmitotic Neurons Or Glia In Vivo In Treatment Of Parkinson's Disease Parkinsonism is a slowly progressive neurodegenerative disease of the central nervous system. Clinical symptoms are tremors at rest, rigidity, akinesia and postural impairment. A hallmark of the disease is reduction of the neurotransmitter dopamine in the basal ganglia which is caused by the loss of nerve cells in the brain stem. These dopamine producing neurons are located in the substantia nigra nucleus of the mesencephalon and project to and terminate in the basal ganglia. Major clinical signs and symptoms arise when around 80% of these neurons are lost.

The administration of the amino acid L-3,4-hydroxyphenylalanine (L-DOPA) is currently the most common treatment of the disease. L-DOPA is the immediate precursor of dopamine and after entering the neuron is converted to dopamine. Remission following this treatment indicates that the remaining dopamine neurons are adequately adaptive to restore basal ganglia activity. However, long term systemic L-DOPA treatments are complicated by side affects.

Amelioration of parkinsonian-like deficits in experimental animal models has also been accomplished by transplantation of fetal dopamine producing cells into the basal ganglia. With the potential ethical, legal, and histocompatibility issues associated with the use of fetal cells, investigators tested the feasibility of using DOPA-secreting cells (chromaffin cells) dissected from the adrenal medulla. Animal experiments in rodents and non-human primates using cells from the adrenal medulla, however, have not been promising because of low survival and immunological rejection (Freed et al., *J. Neurosurg.*, 65:664–670 (1986); Hansen et al., *Exp. Neurol.*, 102:65–75 (1988)). The initial clinical trials with human Parkinson's disease patients also indicate a need for further basic research (Lindvall et al., *Ann. Neuro.*, 22:457–468 (1987; Goetz et al., *N. Engl. J. Med.*, 320:337–341 (1989)). The rate-limiting enzyme tyrosine hydroxylase (TH) is involved in the production of L-DOPA in neurons. The present inventors hypothesize that by increasing levels of TH at the neurons, one can also obtain L-DOPA at the neurons and thus treat Parkinson's disease.

This prophetic example is to stably insert a cDNA which codes for the TH protein into the remaining substantia nigra neurons and in neurons in close proximity to the substantia nigra neurons in the brain stem of patients with Parkinson's disease. The advantage of this gene therapy application is that the TH levels will be elevated in the remaining dopamine neurons of the substantia nigra and in neurons in close proximity to the substantia nigra neurons.

The L-DOPA drug treatments in Parkinson's disease patients have already demonstrated that the remaining dopamine neurons are capable of restoring basal ganglia activity. Instead of elevating the neurotransmitter levels in all the catecholamine/dopamine related pathways which occurs following systemic L-DOPA treatment, this application will elevate the TH levels only in the substantia nigra neurons and in neurons in close proximity to the substantia nigra neurons. The TH levels will be elevated in the specific dopamine producing neurons, which project to and terminate in basal ganglia. As discussed above, a hallmark of Parkinson's disease is reduction of the neurotransmitter dopamine in the basal ganglia.

Immunoliposomes specific for neurons will be made similar to the immunoliposomes of Example 2 except that TH cDNA is substituted for beta-galactosidase cDNA. Moreover, one could design a liposome that is specific for a surface marker of substantia nigra neurons, and thus have a liposome that is even more specific for those particular neurons. Preferably, the liposomes will contain about 10–100 μg of the plasmid DNA (pRcCMV-TH, pRcCMV-PCNA, and pRcCMV-RFC in a 1:1:1 ratio).

Stereotaxic surgery similar to that performed in Example 2 will be performed to inject liposomes containing the inserted plasmids discussed above locally into the area of the substantia nigra neurons of a human or other animal. By selecting the specific area for the injection, one can limit transfection to the substantia nigra neurons and neurons in close proximity to the substantia nigra neurons.

Injecting small volumes of cells into brains of human patients is a rather non-invasive surgery (Lindvall et al. 1987), so injections of liposomes should not be invasive. One skilled in the art will be able to monitor the clinical signs of the patient over time for determine the effective dose and to determine whether subsequent administrations should be provided.

There are additions or alternatives to the above treatment. Given the fact that the Parkinson-like symptoms can be ameliorated in experimental animal models by transplanting dopamine producing cells into cells within the basal ganglia, either glial cells or interneurons in the basal ganglia could be transfected with the similar cDNA constructs and liposome delivery system. One skilled in the art would be aware that the targeted liposomes would be constructed such that they recognize the particular cell type that is to be targeted.

EXAMPLE 4

Stable Integration Of Nerve Growth Factor (NGF) cDNA Into Postmitotic Basal Forebrain Cholinergic Neurons In Alzheimer's Patients Alzheimer's disease is a progressive neurodegenerative disease of the central nervous system resulting in senile dementia. Neuronal populations are differentially affected by the degenerative process with lesions throughout the brain. The entorhinal cortex and hippocampus are severely affected and forebrain cholinergic neurons and brain stem serotinergic and adrenergic neurons which project to the cortex and hippocampus are particularly vulnerable. There are a variety of cellular pathologies including the severally affected cytoskeleton (neurofibrillar tangle) and extracellular deposits of beta-amyloid protein (senile plaques).

It has been proposed that Alzheimers patients be treated with pluripotent neurotrophic factors (Terry, "Regeneration in Alzheimer Disease and Aging," *Advances in Neurology*, Vol. 59, pp. 1–4, Ed. F. J. Seil. Raven Press, Ltd., New York (1993)). There is a family of proteins called neurotrophic factors that have been shown to be responsible for growth and survival of neurons during development (Levi-Montalcine, Science, 237:1154–1162 (1987); Hofer et al., *Nature*, 331:261–261 (1988)) and to prevent death of neurons induced by lesions (Yan et al., *Nature*, 360:753–755 (1992; Koliatosos et al., *Neuron*, 10:359–367 (1993)). In the nervous system, the neurotrophic factors are synthesized and released from other neurons or support cells (glia). These factors bind to specific receptors on neurons, resulting in the activation of metabolic pathways which in turn are responsible for activating the production of proteins involved with growth and survival.

One of the characteristics of the Alzheimer brain is the reduction of cortical acetylcholine which can be caused by atrophy and depletion of nerve-growth-factor dependent (NGF) cholinergic forebrain neurons that project to the cerebral cortex and hippocampus. In animal models, lesion of this cholinergic pathway to the hippocampus results in cell loss in the forebrain cholinergic neurons which can be reversed by NGF (Tuszynski et al., *Ann. Neurol.*, 30:625–636 (1991)). Recombinant human nerve growth factor was infused into the lesion site of the adult primate brain.

In this prophetic example, cDNA encoding NGF protein will be stably inserted into the brain of Alzheimer patients. The source of NGF is Gene Bank Accession No. V01511. The cDNA would be stably inserted into the forebrain where damaged cholinergic neurons are localized. The cDNA constructs using the CMV promoter plasmids and the liposome delivery methods for delivery of the cDNA to the forebrain neurons would be similar to that described in the previous examples above. (NGF cDNA, of course, would be substituted for the TH cDNA.) Moreover, as discussed in Example 3, one skilled in the art would be able to monitor the patient to determine proper dosages and administration schedules.

There is an addition or alternative to this treatment of Alzheimers patients. Since the brain derived neurotrophic factor (BDNF) is at low levels in the hippocampus of Alzheimers patients (Phillips et al., *Neuron*, 7:695–702 (1990)), and since BDNF promotes survival of forebrain cholinergic neurons in vitro (Alderson et al., *Neuron*, 5:297–306 (1990)), cDNA constructs coding for BDNF protein could also be used to transfect hippocampal neurons in Alzheimers patients. The cDNA constructs using the CMV promoter plasmids and the liposome delivery methods for delivery of the cDNA to the hippocampal neurons would be similar to that described in Example 3 above.

What is claimed is:

1. A method for inducing expression of introduced DNA encoding a desired protein in a differentiated cell in vitro comprising:
   obtaining a vectors comprising DNA encoding the desired protein, nucleic acid encoding proliferating cell nuclear antigen (PCNA), and nucleic acid encoding replication factor C (RFC);
   wherein the vectors express the introduced DNA in a differentiated cell; and
   co-transfecting the differentiated cell in vitro with the vectors, whereby expression of the DNA encoding the desired protein is induced.

2. A method for inducing expression of introduced DNA encoding a desired protein in a differentiated cell comprising:
   co-transfecting a differentiated cell in vitro with vectors comprising the introduced DNA encoding the desired protein nucleic acid encoding proliferating cell nuclear antigen (PCNA), and nucleic acid encoding replication factor C (RFC), whereby the introduced DNA encoding the desired protein is expressed in the differentiated cell.

3. A method as in claim 2, wherein the cell is a neuron.

4. A method as in claim 3, further comprising a step inducing repair and recombination in the cell.

5. A method as in claim 3, wherein said transfection step comprises the PCNA, RFC, and the introduced DNA in immunoliposomes.

6. A method for causing a differentiated cell to produce a desired protein comprising:
   co-transfecting a differentiated cell in vitro with, the vectors comprising nucleic acid encoding proliferating cell nuclear antigen (PCNA), nucleic acid encoding replication factor C (RFC), and nucleic acid encoding a desired protein, and expressing the nucleic acid encoding proliferating cell nuclear antigen (PCNA), the nucleic acid encoding replication factor C (RFC), and the nucleic acid encoding the desired protein, thereby causing the cell to produce the desired protein.

7. A method as in claim 6, wherein the cell is a neuron.

8. A method as in claim 7, further comprising inducing DNA repair and recombination in the neuron.

9. A method as in claim 8, wherein said transfection comprises the nucleic acid in immunoliposomes.

10. A method as in claim 8, wherein the desired protein is tyrosine hydroxylase.

11. A method as in claim 8, wherein the desired protein is a neurotrophic factor.

12. A method for transforming a differentiated cell comprising:
   obtaining vectors comprising nucleic acid encoding proliferating cell nuclear antigen (PCNA) and replication factor C (RFC), wherein the vectors express the nucleic acids; and
   co-transfecting a differentiated cell in vitro with the vectors thereby transforming the differentiated cell.

13. A method for inducing expression of a therapeutic protein in a differentiated cell comprising:
   transfecting a differentiated cell in vitro with vectors comprising nucleic acid sequences encoding proliferating cell nuclear antigen (PCNA), replication factor C (RFC), and at least one therapeutic protein, whereby the therapeutic protein is expressed in the cell.

14. A method for inducing expression of messenger RNA encoding the amino acid sequence of a therapeutic protein comprising:
   transfecting a cell in vitro with nucleic acid sequences encoding proliferating cell nuclear antigen (PCNA), replication factor C (RFC), and at least one therapeutic protein, whereby the mRNA for the therapeutic protein is expressed in the cell.

* * * * *